US010463600B2

(12) United States Patent
Plos et al.

(10) Patent No.: US 10,463,600 B2
(45) Date of Patent: Nov. 5, 2019

(54) AEROSOL COMPOSITION COMPRISING A SILICONE FUNCTIONALIZED WITH AT LEAST ONE ALKOXYSILANE UNIT AND AN AMPHOTERIC AND/OR CATIONIC FIXING POLYMER

(71) Applicant: L'OREAL, Paris (FR)

(72) Inventors: Gregory Plos, Paris (FR); Nicolas Daubresse, La Celle Saint-Cloud (FR); Patrice Lerda, Asnieres (FR); Valerie Favreau, Mery-sur-Oise (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/547,142

(22) PCT Filed: Jan. 27, 2016

(86) PCT No.: PCT/EP2016/051696
§ 371 (c)(1),
(2) Date: Jul. 28, 2017

(87) PCT Pub. No.: WO2016/120321
PCT Pub. Date: Aug. 4, 2016

(65) Prior Publication Data
US 2018/0021245 A1    Jan. 25, 2018

(30) Foreign Application Priority Data
Jan. 29, 2015  (FR) ..................... 15 50691

(51) Int. Cl.
*A61K 8/898* (2006.01)
*A61Q 5/06* (2006.01)
*A61K 8/81* (2006.01)
*C08L 83/08* (2006.01)
*A45D 34/00* (2006.01)
*A61K 8/33* (2006.01)
*A61K 8/34* (2006.01)
*B65D 83/14* (2006.01)
*C08L 33/14* (2006.01)

(52) U.S. Cl.
CPC .............. *A61K 8/898* (2013.01); *A45D 34/00* (2013.01); *A61K 8/33* (2013.01); *A61K 8/34* (2013.01); *A61K 8/81* (2013.01); *A61K 8/8152* (2013.01); *A61K 8/8158* (2013.01); *A61Q 5/06* (2013.01); *B65D 83/14* (2013.01); *C08L 83/08* (2013.01); *A61K 2800/5426* (2013.01); *A61K 2800/5428* (2013.01); *A61K 2800/87* (2013.01); *B65D 83/752* (2013.01); *C08L 33/14* (2013.01)

(58) Field of Classification Search
CPC ........ A61K 8/898; A61K 8/81; A61K 8/8152; A61K 8/8158; A61K 8/33; A61K 8/34; A61Q 5/06; C08L 83/08; A45D 34/00; B65D 83/14
See application file for complete search history.

(56) References Cited

U.S. PATENT DOCUMENTS

| 2,047,398 A | 7/1936 | Voss et al. |
| 2,102,113 A | 12/1937 | Djordjevitch |
| 2,723,248 A | 11/1955 | Wright |
| 3,579,629 A | 5/1971 | Pasero et al. |
| 3,589,978 A | 6/1971 | Kamal et al. |
| 3,716,633 A | 2/1973 | Viout et al. |
| 3,810,977 A | 5/1974 | Levine et al. |
| 3,836,537 A | 9/1974 | Boerwinkle et al. |
| 3,910,862 A | 10/1975 | Barabas et al. |
| 3,925,542 A | 12/1975 | Viout et al. |
| 3,946,749 A | 3/1976 | Papantoniou |
| 3,966,403 A | 6/1976 | Papantoniou et al. |
| 3,966,404 A | 6/1976 | Papantoniou et al. |
| 3,990,459 A | 11/1976 | Papantoniou |
| 4,031,307 A | 6/1977 | DeMartino et al. |
| 4,128,631 A | 12/1978 | Lundmark et al. |
| 4,129,711 A | 12/1978 | Viout et al. |
| 4,131,576 A | 12/1978 | Iovine et al. |
| 4,137,208 A | 1/1979 | Elliott |
| 4,165,367 A | 8/1979 | Chakrabarti |
| 4,166,473 A | 9/1979 | Bauer et al. |
| 4,223,009 A | 9/1980 | Chakrabarti |
| 4,282,203 A | 8/1981 | Jacquet et al. |
| 4,289,752 A | 9/1981 | Mahieu et al. |

(Continued)

FOREIGN PATENT DOCUMENTS

| DE | 2330956 A1 | 1/1974 |
| EP | 0080976 A1 | 6/1983 |

(Continued)

OTHER PUBLICATIONS

International Search Report for PCT/EP2016/051697, dated Mar. 21, 2016.
International Search Report for PCT/EP2016/051696, dated Apr. 8, 2016.
International Search Report for PCT/EP2016/051712, dated Mar. 23, 2016.
Todd, Charles, et al., "Volatile Silicone Fluids for Cosmetic Formulations," Cosmetics and Toiletries, vol. 91, Jan. 1976, pp. 29-32.
"Kosmeti sche Zusamrnensetzungen," IP.com Journal, IP.com, Inc., NY, XP013146799, Aug. 4, 2011.
"Table 31; Hair Fixative Polymers Commonly Used in Hair Spray Products ED—Dekker," Hair and Hair Care (Cosmetic Science and Technology)—Series Title: Cosmetic Science and Technology Series, vol. 17, XP007923230, Jan. 1, 1997, pp. 136-137.
Non-Final Office Action for co-pending U.S. Appl. No. 15/547,138, dated May 30, 2019.

(Continued)

*Primary Examiner* — Johann R Richter
*Assistant Examiner* — Genevieve S Alley
(74) *Attorney, Agent, or Firm* — Marbury Law Group, PLLC

(57) ABSTRACT

The present invention relates to an aerosol device comprising a container containing: —one or more propellants, —a hair composition comprising: (i) one or more polymers containing a silicone unit bearing alkoxy-(aminomethyl)-silyl functional groups; (ii) one or more amphoteric fixing polymers and/or one or more cationic fixing polymers; the propellant(s) possibly being present in the composition or, in the container, separate from the composition.

19 Claims, No Drawings

(56) References Cited

U.S. PATENT DOCUMENTS

| | | | |
|---|---|---|---|
| 4,341,229 | A | 7/1982 | Bauer et al. |
| 4,957,732 | A | 9/1990 | Grollier et al. |
| 5,520,199 | A | 5/1996 | Sturla |
| 5,520,200 | A | 5/1996 | Sturla |
| 5,679,324 | A | 10/1997 | Lisboa et al. |
| 8,217,113 | B2 | 7/2012 | Scheim et al. |
| 9,539,199 | B2 | 1/2017 | Beer et al. |
| 2006/0110351 | A1 | 5/2006 | Koehler et al. |
| 2007/0232729 | A1 | 10/2007 | Briehn et al. |
| 2010/0258141 | A1 | 10/2010 | Paul et al. |
| 2010/0307528 | A1 | 12/2010 | Restle et al. |
| 2012/0064018 | A1 | 3/2012 | Schultze et al. |
| 2013/0142750 | A1 | 6/2013 | Fair et al. |
| 2014/0161756 | A1* | 6/2014 | Beer ............ A61Q 5/02 424/70.122 |
| 2014/0245542 | A1 | 9/2014 | Schulze zur Wiesche et al. |
| 2014/0271750 | A1* | 9/2014 | Schulze zur Wiesche ............ A61Q 5/12 424/401 |
| 2015/0104397 | A1 | 4/2015 | Smail et al. |

FOREIGN PATENT DOCUMENTS

| | | |
|---|---|---|
| EP | 0186507 A2 | 7/1986 |
| EP | 0342834 A2 | 11/1989 |
| EP | 0659393 A1 | 6/1995 |
| EP | 0662314 A1 | 7/1995 |
| FR | 1222944 A | 6/1960 |
| FR | 1400366 A | 5/1965 |
| FR | 1564110 A | 4/1969 |
| FR | 1580545 A | 9/1969 |
| FR | 2077143 A | 10/1971 |
| FR | 2198719 A1 | 4/1974 |
| FR | 2265781 A1 | 10/1975 |
| FR | 2265782 A1 | 10/1975 |
| FR | 2273492 A1 | 1/1976 |
| FR | 2350384 A1 | 12/1977 |
| FR | 2357241 A2 | 2/1978 |
| FR | 2393573 A1 | 1/1979 |
| FR | 2439798 A1 | 5/1980 |
| FR | 2990131 A1 | 11/2013 |
| FR | 3008888 A1 | 1/2015 |
| GB | 839805 A | 6/1960 |
| GB | 922457 A | 4/1963 |
| GB | 1021400 A | 3/1966 |
| GB | 1408388 A | 10/1975 |
| GB | 1572626 A | 7/1980 |
| JP | H08-24036 A | 1/1996 |
| JP | H08-24037 A | 1/1996 |
| JP | 2006-249002 A | 9/2006 |
| JP | 2010-241812 A | 10/2010 |
| JP | 2010-540137 A | 12/2010 |
| JP | 2012-516313 A | 7/2012 |
| JP | 2014-523447 A | 9/2014 |
| JP | 2015-500280 A | 1/2015 |
| LU | 75370 A1 | 2/1978 |
| LU | 75371 A1 | 2/1978 |
| WO | 2005/108495 A2 | 11/2005 |
| WO | 2009/019165 A1 | 2/2009 |
| WO | 2013/014140 A2 | 1/2013 |
| WO | 2014/151667 A1 | 9/2014 |
| WO | 2015/011258 A1 | 1/2015 |
| WO | 2016/120322 A1 | 8/2016 |
| WO | 2016/120334 A1 | 8/2016 |

OTHER PUBLICATIONS

Non-Final Office Action for copending U.S. Appl. No. 15/547,166, dated Jan. 31, 2019.

Notification of Reasons for Refusal for counterpart Japanese Application No. 2017-540121, dated Oct. 29, 2018.

* cited by examiner

AEROSOL COMPOSITION COMPRISING A SILICONE FUNCTIONALIZED WITH AT LEAST ONE ALKOXYSILANE UNIT AND AN AMPHOTERIC AND/OR CATIONIC FIXING POLYMER

CROSS REFERENCE TO RELATED APPLICATIONS

This is a national stage application of PCT/EP2016/051696, filed internationally on Jan. 27, 2016, which claims priority to French Application No. 1550691, filed on Jan. 29, 2015, both of which are incorporated by reference herein in their entireties.

The present invention relates to an aerosol device containing a hair composition comprising one or more particular silicones and one or more amphoteric and/or cationic fixing polymers. The present invention also relates to a process for shaping and/or holding the hairstyle using said device.

In the field of styling, in particular among hair products intended for shaping and/or holding the hairstyle, the hair compositions that are the most widespread on the cosmetics market are compositions consisting essentially of a solution, which is usually alcoholic or aqueous-alcoholic, and of one or more polymers, known as fixing polymers, which are generally film-forming polymers. These polymers thus have the function of making welds between the hairs so as to be able to structure the hairstyle and give it long-lasting hold.

However, certain fixing polymers result in hardening of the head of hair. This drawback leads to a set hairstyle and to disentangling that is often difficult at the end of the day, the hair having a dry feel.

To improve the cosmetic feel of the hair, it is known practice to add silicone or oxyethylene compounds. However, this type of combination has a tendency to reduce the level of fixing of the compositions and to reduce the hairstyle hold.

However, these products are not entirely satisfactory, especially in terms of the balance between the fixing power and the cosmetic qualities of the head of hair, and especially the feel of the hair during drying, immediately after application and after removal by brushing. Either a very high level of fixing is obtained with a product which appears as tacky during drying, and then rigid, dry, or even coarse, or a feel is obtained that remains relatively natural, but with a low level of fixing.

There is thus a real need to find compositions, especially for hairstyling, which allow a good level of fixing and long-lasting hairstyle hold while at the same time giving the hair a cosmetic feel.

The Applicant has found, surprisingly and unexpectedly, that the combination of one or more polymers containing a silicone unit bearing alkoxy-(aminomethyl)-silyl functional groups and one or more amphoteric and/or cationic fixing polymers in an aerosol device makes it possible to obtain a head of hair that does not have the above drawbacks.

Specifically, this combination makes it possible to obtain strong fixing of the head of hair, which lasts throughout the day, while at the same time giving the hair a cosmetic feel. The hair is held in the desired shape without being set or hardened by the sprayed composition, the hair being soft, supple and smooth.

One subject of the invention is thus an aerosol device comprising a container containing:

one or more propellants,
a hair composition comprising:
    (i) one or more polymers containing a silicone unit bearing alkoxy-(aminomethyl)-silyl functional groups;
    (ii) one or more amphoteric fixing polymers and/or one or more cationic fixing polymers;
the propellant(s) possibly being present in the composition or, in the container, separate from the composition.

Another subject of the present invention consists of a process for shaping and/or holding the hairstyle using the device according to the invention.

Other subjects, characteristics, aspects and advantages of the invention will emerge even more clearly on reading the description and the example that follows.

According to the invention, the aerosol device comprises a container which contains a hair composition comprising (i) one or more polymers containing a silicone unit bearing alkoxy-(aminomethyl)-silyl functional groups; and (ii) one or more amphoteric fixing polymers and/or one or more cationic fixing polymers.

The composition of the invention comprises one or more polymers containing a silicone unit bearing alkoxy-(aminomethyl)-silyl functional groups.

The polymer(s) containing a silicone unit bearing alkoxy-(aminomethyl)-silyl functional groups are preferably of formula (I) below:

$$Z_2-\underset{\underset{Z_3}{|}}{\overset{\overset{O-R_1}{|}}{Si}}-O-\underset{\underset{R_b}{|}}{\overset{\overset{R_a}{|}}{Si}}-O-\left[\underset{\underset{R_b}{|}}{\overset{\overset{R_a}{|}}{Si}}-O\right]_n-\underset{\underset{Z_3}{|}}{\overset{\overset{R_1\diagdown O}{|}}{Si}}-Z_2 \qquad (I)$$

in which:
$Z_2$ represents a group $-CH_2-NR_3R_4$;
$Z_3$ represents a group $OR_5$ or $R_6$;
$R_1$ represents a $C_1$-$C_6$ alkyl group,
    $R_3$ represents a hydrogen atom or a group $R_7$; $R_4$ represents a $C_1$-$C_6$ alkyl group or a $C_5$-$C_6$ cycloalkyl group; or
    $R_3$ and $R_4$ possibly forming, with the nitrogen atom that bears them, a 5- to 8-membered heterocycle comprising from 1 to 3 heteroatoms,
$R_5$, $R_6$ and $R_7$, which may be identical or different, represent a $C_1$-$C_6$ alkyl group, and
$R_a$ and $R_b$, which may be identical or different, represent a $C_1$-$C_2$ alkyl group,
n represents an integer greater than 1.

Preferably, the $C_1$-$C_6$ alkyl groups are methyl or ethyl groups.

Preferably, $R_1$ is an ethyl group.

When $R_4$ represents a $C_5$-$C_6$ cycloalkyl group, it preferably represents a $C_6$ cycloalkyl group such as cyclohexyl.

Preferably, n ranges from 1 to 10 000, preferably from 5 to 1000 and even more preferably from 8 to 400.

According to a particular embodiment of the invention, $Z_2$ represents a group $-CH_2-NR_3R_4$, $R_4$ represents an alkyl group, preferably a cyclohexyl, $R_3$ represents a hydrogen atom and $R_5$ represents an ethyl group.

According to a particular embodiment of the invention, $Z_2$ represents a group $-CH_2-NR_3R_4$, $R_4$ represents an alkyl group, preferably a cyclohexyl, $R_3$ represents a hydrogen atom and $R_5$ represents an ethyl group.

Preferably, in formula (I), $SiR_aR_b$—$[OSiR_aR_b]n$- is a unit derived from a linear silicone with a weight-average molecular mass (Mw) ranging from 200 to 40 000 and more preferentially from 400 to 25 000 g/mol.

As examples of polymers used in the process of the invention, mention will be made of:

polymers of formula (Ia)

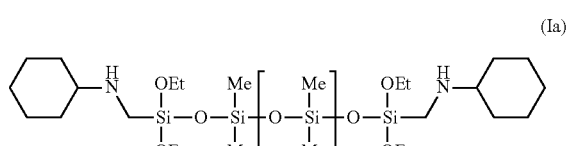

The polymers of formula (Ia) may be obtained by reacting a silicone bearing hydroxyl end groups with triethoxycyclohexylaminomethylsilane especially according to the techniques described in WO 2005/108 495.

According to a particular example, polymer (Iaa), corresponding to formula (Ia), is obtained according to the operating scheme presented above, starting with a silicone with a weight-average molecular mass Mw of 4750 g/mol.

polymers of formula (Ib)

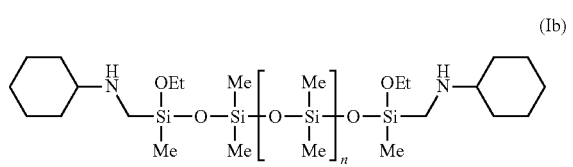

The polymers of formula (Ib) may be obtained by reacting a silicone bearing hydroxyl end groups with diethoxycyclohexylaminomethylmethylsilane especially according to the techniques described in WO 2005/108 495.

According to a particular example, polymer (Iba), corresponding to formula (Ib), is obtained according to the operating scheme presented above, starting with a silicone with a weight-average molecular mass Mw of 4750 g/mol.

polymers of formula (Ic)

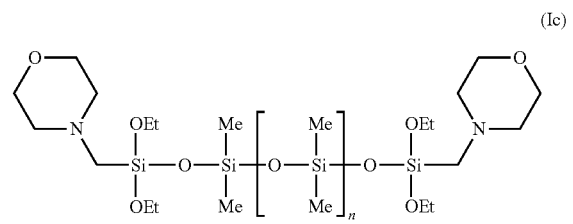

The polymers of formula (Ic) may be obtained by reacting a silicone bearing hydroxyl end groups with triethoxymorpholinomethylsilane especially according to the techniques described in WO 2009/019 165.

According to a particular example, polymer (Ica), corresponding to formula (Ic), is obtained according to the operating scheme presented above, starting with a silicone with a weight-average molecular mass Mw of 4750 g/mol.

According to another particular example, polymer (Icb), corresponding to formula (Ic), is obtained according to the operating scheme presented above, starting with a silicone with a weight-average molecular mass of 10 600 g/mol.

According to another particular example, polymer (Icc), corresponding to formula (Ic), is obtained according to the operating scheme presented above, starting with a silicone with a weight-average molecular mass of 14 600 g/mol.

According to another particular example, polymer (Icd), corresponding to formula (Ic), is obtained according to the operating scheme presented above, starting with a silicone with a weight-average molecular mass Mw of 21 100 g/mol.

According to another particular example, polymer (Ice), corresponding to formula (Ic), is obtained according to the operating scheme presented above, starting with a silicone with a weight-average molecular mass Mw of 550 g/mol.

According to another particular example, polymer (Icf), corresponding to formula (Ic), is obtained according to the operating scheme presented above, starting with a silicone with a weight-average molecular mass Mw of 1000 g/mol.

According to another particular example, polymer (Icg), corresponding to formula (Ic), is obtained according to the operating scheme presented above, starting with a silicone with a weight-average molecular mass Mw of 1200 g/mol.

According to another particular example, polymer (Ich), corresponding to formula (Ic), is obtained according to the operating scheme presented above, starting with a silicone with a weight-average molecular mass Mw of 1700 g/mol.

polymers of formula (Id)

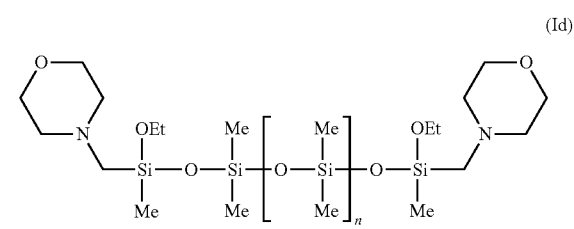

The polymers of formula (Id) may be obtained by reacting a silicone bearing hydroxyl end groups with diethoxymorpholinomethylmethylsilane especially according to the techniques described in document WO 2009/019 165.

According to a particular example, the polymer of formula (Ida), corresponding to formula (Id), is obtained according to the operating scheme presented above, starting with a silicone with a weight-average molecular mass Mw of 4750 g/mol.

According to another particular example, the polymer of formula (Idb), corresponding to formula (Id), is obtained according to the operating scheme presented above, starting with a silicone with a weight-average molecular mass Mw of 10 600 g/mol.

According to another particular example, the polymer of formula (Idc), corresponding to formula (Id), is obtained according to the operating scheme presented above, starting with a silicone with a weight-average molecular mass Mw of 14 600 g/mol.

According to a particular example, the polymer of formula (Idd), corresponding to formula (Id), is obtained according to the operating scheme presented above, starting with a silicone with a weight-average molecular mass Mw of 21 100 g/mol.

The content of the polymer(s) containing a silicone unit bearing alkoxy-(aminomethyl)-silyl functional groups, preferably of formula (I), in the composition containing them generally ranges from 0.1% to 40% by weight, preferably from 0.5% to 30% by weight and more particularly from 1% to 10% by weight relative to the total weight of the composition in which they are used.

The composition of the invention also comprises one or more cationic fixing polymers and/or one or more amphoteric fixing polymers.

For the purposes of the invention, the term "fixing polymer" means any polymer that is capable, by application to the hair, of giving a shape to a head of hair or of holding the hair in an already acquired shape.

The cationic fixing polymers that may be used according to the present invention are preferably chosen from polymers comprising primary, secondary, tertiary and/or quaternary amine groups forming part of the polymer chain or directly attached thereto, and having a molecular weight of between 500 and approximately 5 000 000 and preferably between 1000 and 3 000 000.

Mention may more particularly be made, among these polymers, of the following cationic polymers:

(1) homopolymers or copolymers derived from acrylic or methacrylic esters or amides and comprising at least one of the units of the following formulae:

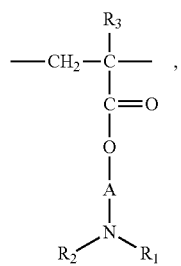

(A)

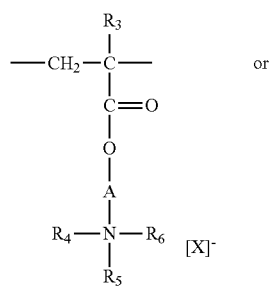

(B)

or

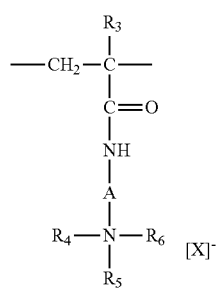

(C)

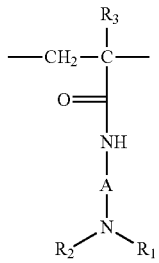

(D)

in which:
R₁ and R₂, which may be identical or different, represent a hydrogen atom or an alkyl group containing from 1 to 6 carbon atoms;
R₃, which may be identical or different in each formula, denotes a hydrogen atom or a CH₃ radical;
A, which may be identical or different in each formula, denotes a linear or branched alkyl group comprising from 1 to 6 carbon atoms or a hydroxyalkyl group comprising from 1 to 4 carbon atoms;
R₄, R₅ and R₆, which may be identical or different in each formula, represent an alkyl group containing from 1 to 18 carbon atoms or a benzyl radical;
X⁻ denotes a methosulfate anion or a halide such as chloride or bromide.

The copolymers of class (1) also contain one or more units derived from comonomers which may be chosen from the class of acrylamides, methacrylamides, diacetone acrylamides, acrylamides and methacrylamides substituted on the nitrogen with C₁-C₄ alkyl groups, groups derived from acrylic or methacrylic acids or esters thereof, vinyllactams such as vinylpyrrolidone or vinylcaprolactam, and vinyl esters.

Thus, among these copolymers of class (1), mention may be made of:
copolymers of acrylamide and of dimethylaminoethyl methacrylate which is quaternized with dimethyl sulfate or with a dimethyl halide, such as that sold under the name Hercofloc® by the company Hercules,
copolymers of acrylamide and of methacryloyloxyethyltrimethylammonium chloride, described for example in patent application EP-A-080976 and sold under the name Bina Quat P 100 by the company Ciba Geigy,
the copolymer of acrylamide and of methacryloyloxyethyltrimethylammonium methosulfate, such as that sold under the name Reten by the company Hercules,
quaternized or non-quaternized vinylpyrrolidone/dialkylaminoalkyl acrylate or methacrylate copolymers, such as the products sold under the name Gafquat® by the company ISP, for instance Gafquat® 734 or Gafquat® 755, or alternatively the products known as Copolymer® 845, 958 and 937. These polymers are described in detail in French patents 2 077 143 and 2 393 573,
polymers comprising a fatty chain and comprising a vinylpyrrolidone unit, such as the products sold under the names Styleze W20 and Styleze W10 by the company ISP,
dimethylaminoethyl methacrylate/vinylcaprolactam/vinylpyrrolidone terpolymers, such as the product sold under the name Gaffix VC 713 by the company ISP, and
quaternized vinylpyrrolidone/dimethylaminopropylmethacrylamide copolymers, such as the products sold under the name Gafquat® HS 100 by the company ISP.

(2) cationic guar gums, preferably containing quaternary ammonium, such as those described in U.S. Pat. No. 3,589,578 and 4 031 307, such as guar gums containing trialkylammonium cationic groups. Such products are sold especially under the trade names Jaguar C13S, Jaguar C15 and Jaguar C17 by the company Meyhall.

(3) quaternary copolymers of vinylpyrrolidone and of vinylimidazole;

(4) chitosans or salts thereof; the salts that may be used are in particular the acetate, lactate, glutamate, gluconate or pyrrolidonecarboxylate of chitosan.

Among these compounds, mention may be made of chitosan having a degree of deacetylation of 90.5% by weight, sold under the name Kytan Brut Standard by the company Aber Technologies, and chitosan pyrrolidonecarboxylate sold under the name Kytamer® PC by the company Amerchol.

(5) cationic cellulose derivatives, such as copolymers of cellulose or of cellulose derivatives grafted with a water-soluble monomer comprising a quaternary ammonium and described especially in U.S. Pat. No. 4,131,576, such as hydroxyalkylcelluloses, for instance hydroxymethyl-, hydroxyethyl- or hydroxypropylcelluloses, grafted especially with a methacryloyloxyethyltrimethylammonium, methacrylamidopropyltrimethylammonium or dimethyldiallylammonium salt. The commercial products corresponding to this definition are more particularly the products sold under the names Celquat L 200 and Celquat H 100 by the company National Starch.

(6) optionally partially or totally neutralized vinylamine and N-vinylformamide copolymers.

The amphoteric fixing polymers that may be used in accordance with the invention may be chosen from polymers comprising units B and C distributed randomly in the polymer chain, in which B denotes a unit derived from a monomer comprising at least one basic nitrogen atom and C denotes a unit derived from an acid monomer comprising one or more carboxylic or sulfonic groups, or alternatively B and C may denote groups derived from carboxybetaine or sulfobetaine zwitterionic monomers; B and C may also denote a cationic polymer chain comprising primary, secondary, tertiary or quaternary amine groups, in which at least one of the amine groups bears a carboxylic or sulfonic group connected via a hydrocarbon-based group, or alternatively B and C form part of a chain of a polymer containing an ethylenedicarboxylic unit in which one of the carboxylic groups has been made to react with a polyamine comprising one or more primary or secondary amine groups.

The amphoteric polymers corresponding to the definition given above that are more particularly preferred are chosen from the following polymers:

1) polymers resulting from the copolymerization of a monomer derived from a vinyl compound bearing a carboxylic group, such as, more particularly, acrylic acid, methacrylic acid, maleic acid or α-chloroacrylic acid, and of a basic monomer derived from a substituted vinyl compound containing at least one basic atom, such as, more particularly, dialkylaminoalkyl methacrylate and acrylate, and dialkylaminoalkylmethacrylamide and -acrylamide. Such compounds are described in US patent No. 3,836,537.

The vinyl compound may also be a dialkyldiallylammonium salt such as diethyldiallylammonium chloride.

2) polymers comprising units derived:

a) from at least one monomer chosen from acrylamides or methacrylamides substituted on the nitrogen with an alkyl group, b) from at least one acidic comonomer containing one or more reactive carboxylic groups, and c) from at least one basic comonomer such as acrylic and methacrylic acid esters containing primary, secondary, tertiary and quaternary amine substituents, and the product of quaternization of dimethylaminoethyl methacrylate with dimethyl or diethyl sulfate.

The N-substituted acrylamides or methacrylamides that are more particularly preferred according to the invention are compounds in which the alkyl groups contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are more particularly chosen from acrylic acid, methacrylic acid, crotonic acid, itaconic acid, maleic acid and fumaric acid and alkyl monoesters, containing 1 to 4 carbon atoms, of maleic or fumaric acids or anhydrides. The preferred basic comonomers are aminoethyl, butylaminoethyl, N,N'-dimethylaminoethyl and N-(tert-butyl)aminoethyl methacrylates. The copolymers of which the CTFA (4th edition, 1991) name is octylacrylamide/acrylates/butylaminoethyl methacrylate copolymer, such as the products sold under the name Amphomer® or Lovocryl® 47 by the company National Starch, are particularly used.

(3) crosslinked and alkylated polyamino amides partially or totally derived from polyamino amides of general formula:

 (II)

in which $R_4$ represents a divalent group derived from a saturated dicarboxylic acid, from a mono- or dicarboxylic aliphatic acid with an ethylenic double bond, from an ester of an alcohol having 1 to 6 carbon atoms with these acids, or from a group deriving from the addition of any one of said acids with a bis-primary amine or bis-secondary-derived amine, and Z denotes a group of a bis-primary or mono- or bis-secondary polyalkylene-polyamine, and preferably represents:

a) in proportions of from 60 mol % to 100 mol %, the group

 (III)

where x=2 and p=2 or 3, or else x=3 and p=2, this group deriving from diethylenetriamine, triethylenetetramine or dipropylenetriamine;

b) in proportions of from 0 to 40 mol %, the group (III) above, in which x=2 and p=1, which derives from ethylenediamine, or the group deriving from piperazine

c) in proportions of from 0 to 20 mol %, the —NH—(CH2)6-NH— group deriving from hexamethylenediamine, these polyaminoamines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyaminoamide and alkylated by the action of acrylic acid, chloroacetic acid or an alkane sultone, or salts thereof.

The saturated carboxylic acids are preferably chosen from acids containing 6 to 10 carbon atoms, such as adipic acid, 2,2,4-trimethyladipic acid, 2,4,4-trimethyladipic acid and terephthalic acid, and acids having an ethylenic double bond, such as, for example, acrylic, methacrylic and itaconic acids. The alkane sultones used in the alkylation are preferably propane sultone or butane sultone; the salts of the alkylating agents are preferably the sodium or potassium salts.

4) polymers containing zwitterionic units of formula:

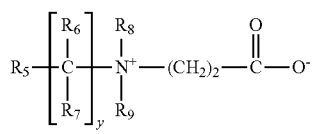
(IV)

in which $R_5$ denotes a polymerizable unsaturated group, such as an acrylate, methacrylate, acrylamide or methacrylamide group, y and z each represent an integer from 1 to 3, $R_6$ and $R_7$ represent a hydrogen atom or a methyl, ethyl or propyl group, $R_8$ and $R_9$ represent a hydrogen atom or an alkyl group such that the sum of the carbon atoms in $R_{10}$ and $R_{11}$ does not exceed 10.

The polymers comprising such units may also comprise units derived from non-zwitterionic monomers such as dimethyl- or diethylaminoethyl acrylate or methacrylate or alkyl acrylates or methacrylates, acrylamides or methacrylamides or vinyl acetate.

5) polymers derived from chitosan comprising monomer units corresponding to the following formulae:

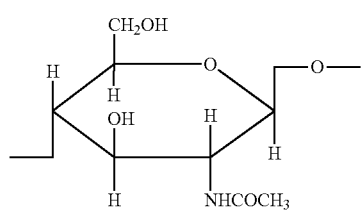
(V)

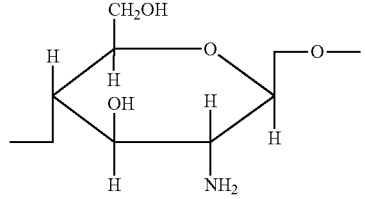
(VI)

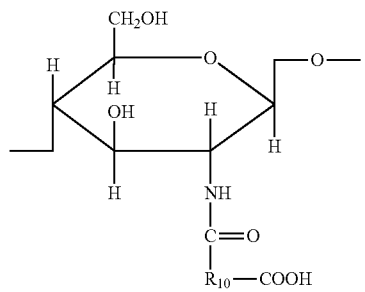
(VII)

the unit (V) being present in proportions of between 0 and 30%, the unit (VI) in proportions of between 5% and 50% and the unit (VII) in proportions of between 30% and 90%, it being understood that, in this unit F, $R_{10}$ represents a group of formula:

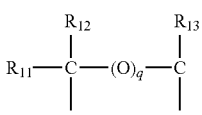
(VIII)

in which, if q=0, $R_{11}$, $R_{12}$ and $R_{13}$, which may be identical or different, each represent a hydrogen atom, a methyl, hydroxyl, acetoxy or amino residue, a monoalkylamine residue or a dialkylamine residue that are optionally interrupted with one or more nitrogen atoms and/or optionally substituted with one or more amine, hydroxyl, carboxyl, alkylthio or sulfonic groups, an alkylthio residue in which the alkyl group bears an amino residue, at least one of the groups $R_{17}$, $R_{18}$ and $R_{19}$ being, in this case, a hydrogen atom;

or, if q=1, $R_{11}$, $R_{12}$ and $R_{13}$ each represent a hydrogen atom, and also the salts formed by these compounds with bases or acids.

6) polymers derived from the N-carboxyalkylation of chitosan.

7) polymers of units corresponding to general formula (IX), described, for example, in French patent 1 400 366:

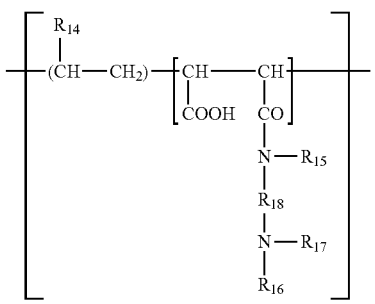
(IX)

in which $R_{14}$ represents a hydrogen atom or a $CH_3O$, $CH_3CH_2O$, or phenyl group, $R_{15}$ denotes hydrogen or a $C_1$-$C_4$ alkyl group such as methyl and ethyl, $R_{16}$ denotes hydrogen or a $C_1$-$C_4$ alkyl group such as methyl and ethyl, $R_{17}$ denotes a $C_1$-$C_4$ alkyl group such as methyl and ethyl or a group corresponding to the formula: $—R_{18}—N(R_{16})_2$, with $R_{18}$ representing a $—CH_2—CH_2—$, $—CH_2—CH_2—CH_2—$, or $—CH_2—CH(CH_3)—$ group and $R_{16}$ having the meanings given above, and also the higher homologues of these groups, containing up to 6 carbon atoms.

8) amphoteric polymers of the type -D-X-D-X—, chosen from:

a) polymers obtained by the action of chloroacetic acid or sodium chloroacetate on compounds comprising at least one unit of formula:

-D-X-D-X-D- (X)

where D denotes a group

and X denotes the symbol E or E', where E or E', which may be identical or different, denote a divalent group that is an alkylene group with a straight or branched chain containing up to 7 carbon atoms in the main chain, which is unsubstituted or substituted with hydroxyl groups and which can comprise, in addition to oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups.

b) polymers of formula:

-D-X-D-X— (XI)

where D denotes a group

and X denotes the symbol E or E' and at least once E'; E having the meaning given above and E' is a divalent group that is an alkylene group with a straight or branched chain containing up to 7 carbon atoms in the main chain, which is unsubstituted or substituted with one or more hydroxyl groups and which contains one or more nitrogen atoms, the nitrogen atom being substituted with an alkyl chain that is optionally interrupted with an oxygen atom and necessarily comprises one or more carboxyl functions or one or more hydroxyl functions, betainized by reaction with chloroacetic acid or sodium chloroacetate.

9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers may also comprise other vinyl comonomers such as vinylcaprolactam.

According to a preferred embodiment of the invention, the amphoteric fixing polymers that may be used in the aerosol device according to the invention may be chosen from branched block copolymers comprising:

(a) nonionic units derived from at least one monomer chosen from $C_1$-$C_{20}$ alkyl (meth)acrylates, N-mono-($C_2$-$C_{12}$ alkyl)(meth)acrylamides and N,N-di($C_2$-$C_{12}$ alkyl)(meth)acrylamides, (b) anionic units derived from at least one monomer chosen from acrylic acid and methacrylic acid, and (c) polyfunctional units derived from at least one monomer containing at least two polymerizable unsaturated functional groups, and preferably having a structure constituted of hydrophobic blocks onto which are fixed, via polyfunctional units (c), several blocks which are more hydrophilic.

Preferably, the amphoteric polymers have at least two glass transition temperatures (Tg), at least one of which is greater than 20° C. and the other of which is less than 20° C.

The preferred amphoteric polymers are polymers comprising units deriving:

a) from at least one monomer chosen from acrylamides or methacrylamides substituted on the nitrogen with an alkyl group, b) from at least one acidic comonomer containing one or more reactive carboxylic groups, and c) from at least one basic comonomer such as acrylic and methacrylic acid esters containing primary, secondary, tertiary and quaternary amine substituents, and the product of quaternization of dimethylaminoethyl methacrylate with dimethyl or diethyl sulfate.

Mention may be made in particular of the polymers sold under the name Amphomer® by the company Akzo Nobel.

Preferably, the composition comprises at least one amphoteric fixing polymer.

The cationic and/or amphoteric fixing polymer(s) are preferably present in an amount ranging from 0.5% to 20% by weight and preferably from 1% to 10% relative to the total weight of the composition in which they are used.

The composition according to the invention may also comprise one or more catalysts for catalysing the hydrolysis-condensation reactions of the alkoxysilane functions of the polymer containing a silicone unit bearing alkoxy-(aminomethyl)-silyl functional groups.

The catalyst may be chosen from acids and bases.

The acid may be chosen from mineral acids and organic acids.

The acid may be chosen in particular from lactic acid, acetic acid, citric acid, tartaric acid, hydrochloric acid, sulfuric acid and phosphoric acid, preferably hydrochloric acid.

The base may be chosen from mineral bases and organic bases.

The base may be chosen from ammonia and sodium hydroxide.

According to a particular embodiment, it is possible for the catalyst not to be present in the composition and to be mixed at the time of use with the composition comprising the polymer(s) containing a silicone unit bearing alkoxy-(aminomethyl)-silyl functional groups, or alternatively may be applied sequentially to the hair before or after the composition comprising the polymer(s) containing a silicone unit bearing alkoxy-(aminomethyl)-silyl functional groups.

The catalyst(s) may represent from 0.0001% to 10% by weight, preferably from 0.001% to 5% by weight and more particularly from 0.01% to 2% by weight relative to the total weight of the composition containing them, when the propellant(s) are present in the composition.

The composition may be aqueous or anhydrous. When it contains any, the composition preferably contains less than 5% by weight of water relative to the total weight of the composition.

The composition is preferably anhydrous. For the purposes of the present invention, the term "anhydrous composition" means a composition having a water content of less than 3% by weight, preferably less than 2% by weight relative to the total weight of the composition, and/or a composition which does not contain any added water, i.e. the water that may be present in the composition according to the invention is more particularly bound water, such as the water of crystallization of salts, or traces of water absorbed by the starting materials used in the production of the compositions.

The composition(s) according to the invention may comprise one or more organic solvents, preferably chosen from alcohols, alkanes, esters and silicones, and mixtures thereof.

The alcohols are linear or branched $C_1$-$C_6$ monoalcohols or polyols.

The esters may be natural or synthetic.

The esters may be chosen especially from plant oils and esters of fatty acids or of fatty alcohols, such as isopropyl myristate.

The alkanes may be chosen especially from linear or branched $C_6$-$C_{15}$ alkanes and liquid paraffins.

The silicones may be chosen especially from cyclic silicones comprising from 4 to 6 silicon atoms and linear polydimethylsiloxanes.

Preferably, the organic solvent is chosen from ethanol, propanol, isopropanol, glycerol, undecane, tridecane, isododecane, isopropyl myristate, ethyl adipate, ethyl acetate, linear low-molecular-weight silicones or cyclic silicones such as cyclopentasiloxane, and also mixtures thereof.

According to a preferred embodiment, the solvent is chosen from ethanol and isopropanol, and mixtures thereof.

The organic solvents that may be used in the composition of the invention are liquids that preferably have a viscosity at 25° C. and at atmospheric pressure of less than or equal to 100 cSt.

When they are present, the organic solvent(s) may represent from 10% to 99.8%, preferably from 30% to 98% by weight and better still from 35% to 95% by weight relative to the total weight of the composition containing them when the propellant(s) are present in the composition.

The container of the device according to the invention also comprises one or more propellants.

Examples of propellants that may be used in the aerosol device of the present invention are liquefied gases such as dimethyl ether, chlorinated and/or fluorinated hydrocarbons such as 1,1-difluoroethane, or volatile hydrocarbons especially such as $C_3$-$C_5$ alkanes, for instance propane, isopropane, n-butane, isobutane or pentane, or compressed gases such as air, nitrogen or carbon dioxide, and mixtures thereof.

Mention may be made preferentially of dimethyl ether and $C_{3-5}$ alkanes and in particular propane, n-butane and isobutane, and mixtures thereof.

The propellant(s) may be present in the composition or, as a variant, in the container containing the composition, but separate from the composition.

The agent(s) are preferably present in the composition.

When the propellant(s) are present in the composition, they are preferably present in an amount ranging from 10% to 90% by weight, even better still from 15% to 80% by weight and even more preferentially from 20% to 75% by weight relative to the total weight of the composition.

The compositions defined in the invention may also contain one or more additives chosen from plasticizers, surfactants, and in particular nonionic and/or phosphate-based surfactants, silicones, fatty esters, fatty alcohols, anionic, cationic, nonionic, amphoteric or zwitterionic polymers other than the fixing polymers, fragrances, dyes, UV-protective screening agents, acids, bases, nacres and glitter flakes.

These additives may be present in the composition according to the invention in an amount ranging from 0 to 20% by weight, relative to the total weight of the composition, when the propellant(s) are present in the composition.

A person skilled in the art will take care to select these optional additives and amounts thereof so that they do not harm the properties of the compositions of the present invention.

The composition(s) may be in the form of a solution, a dispersion or an emulsion. The polymer containing a silicone unit bearing alkoxy-(aminomethyl)-silyl functional groups may be emulsified as an oil-in-water or water-in-oil emulsion or as a multiple emulsion.

The composition of the invention may be in the form of a foam or a lacquer. In the case of aerosol foams, the composition introduced into the aerosol device may, for example, be in the form of a lotion, or a dispersion or an emulsion which, after dispensing from the aerosol device, forms a foam to be applied to the hair.

These foams are preferably sufficiently stable so as not to liquefy rapidly and preferably must also disappear rapidly, either spontaneously or during the massaging which serves to make the composition penetrate into keratin materials and/or to distribute the composition on the keratin materials and more particularly the head of hair and/or the hair.

In the case of aerosol foams, the composition may also contain at least one cationic, nonionic, anionic or amphoteric surfactant.

Preferably, the composition is in the form of a lacquer.

As already mentioned previously, the container contains both the propellant(s) and the other ingredients of the composition, in a single compartment, or as a variant in two compartments. According to the latter variant, the container may be constituted of an outer aerosol can comprising an inner bag hermetically welded to a valve. The various ingredients of the composition are introduced into the inner bag and a propellant is introduced between the bag and the can at a sufficient pressure to make the product come out in the form of a spray.

The container is equipped at its top end with a valve that seals the system.

Onto this valve is fitted a dispensing means, on which the user can press to make the product come out. This dispensing means is also known as a diffuser. It may comprise a single spray orifice, for example with a direct or turbulent-channel outlet. As a variant, it may comprise several spray orifices.

The invention also relates to a process for shaping and/or holding the hairstyle, which consists in applying to the hair the composition described previously by means of the device that has just been described.

According to a particular embodiment, the application may be performed in a single stage. In this case, a composition including one or more polymers containing a silicone unit bearing alkoxy-(aminomethyl)-silyl functional groups, preferably of formula (I), one or more amphoteric fixing polymers and/or one or more cationic fixing polymers, and optionally one or more catalysts as defined previously, will be applied by spraying.

In this one-stage embodiment, the composition sprayed onto the hair may result from the mixing of a composition comprising one or more polymers containing a silicone unit bearing alkoxy-(aminomethyl)-silyl functional groups, preferably of formula (I), and one or more amphoteric fixing polymers and/or one or more cationic fixing polymers, and of a composition comprising one or more catalysts as defined previously.

According to another embodiment, the application may be performed in two stages: in a step (A) the composition comprising one or more catalysts as defined previously is applied, in a step (B) the composition comprising one or more polymers containing a silicone unit bearing alkoxy-(aminomethyl)-silyl functional groups, preferably of formula (I), and one or more amphoteric fixing polymers and/or one or more cationic fixing polymers is applied by spraying.

In this embodiment, step (A) may be performed, followed by step (B), or alternatively step (B) may be performed, followed by step (A), with or without intermediate drying. Preferably, step (A) is performed, followed by step (B). In this particular embodiment, intermediate drying is preferably performed.

The invention is illustrated in greater detail in the examples that follow, which are given as non-limiting illustrations of the invention.

EXAMPLE

Composition A according to the invention and composition B were prepared from the ingredients indicated in the table below, in grams of active material:

|  | A invention | B control |
|---|---|---|
| Polymer Ic (MW = 13 100) | 2.2 | — |
| Octylacrylamide/acrylates/butylaminoethyl methacrylate copolymer [(1)] | 4.4 | 4.4 |
| Dimethyl ether | 45 | 45 |
| Isopropanol | qs 100 | qs 100 |

[(1)] Sold under the trade name Amphomer® by Akzo Nobel

The compositions prepared above were introduced into an aerosol dispensing device which has the following characteristics:
 a valve equipped with a nozzle with an orifice 0.41 mm in size and an internal orifice 2.03 mm in size,
 a diffuser equipped with a turbulent-channel nozzle whose orifice is 0.38 mm in diameter.

1.5 g of these aerosol compositions were sprayed onto 5.4 g locks of dry hair laid out in a fan shape (spraying on both sides).

A level of fixing with composition A according to the invention equivalent to that obtained with composition B is obtained. The fixing is also longer-lasting with composition A according to the invention than with composition B. The fixing hold in wet medium is also improved with composition A according to the invention relative to composition B.

Moreover, a much smoother feel of the hair is obtained from the start of drying of composition A, and even more so after drying.

The invention claimed is:

1. An aerosol device comprising:
 a container, wherein the container comprises:
 at least one propellant; and
 a hair composition, the composition comprising:
 (i) at least one polymer containing a silicone unit bearing alkoxy-(aminomethyl)-silyl functional groups chosen from compounds according to formula (I) below:

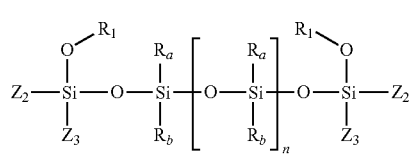

(I)

wherein:
 $Z_2$ is chosen from —$CH_2$—$NR_3R_4$ groups;
 $Z_3$ is chosen from $OR_5$ or $R_6$ groups;
 $R_1$ is chosen from $C_1$-$C_6$ alkyl groups;
 $R_3$ is chosen from a hydrogen atom or an $R_7$ group;
 $R_4$ is chosen from $C_1$-$C_6$ alkyl groups or $C_5$-$C_6$ cycloalkyl groups; or $R_3$ and $R_4$, optionally form, with the nitrogen atom that bears them, a 5- to 8-membered heterocycle comprising from 1 to 3 heteroatoms;
 $R_5$, $R_6$, and $R_7$, which may be identical or different, are chosen from $C_1$-$C_6$ alkyl groups;
 $R_a$ and $R_b$, which may be identical or different, are chosen from $C_1$-$C_2$ alkyl groups; and
 n is an integer greater than 1; and
 (ii) at least one amphoteric fixing polymer and/or at least one cationic fixing polymer;
 wherein the at least one propellant is present in the composition, or in the container, separate from the composition.

2. The device according to claim 1, wherein the $C_1$-$C_6$ alkyl groups are chosen from methyl or ethyl groups.

3. The device according to claim 1, wherein $R_3$ and $R_4$ form, with the nitrogen atom that bears them, a 5- to 8-membered heterocycle comprising from 1 to 3 heteroatoms; and
 $R_1$, $R_5$, and $R_6$ are chosen from methyl or ethyl groups.

4. The device according to claim 1, wherein $R_3$ and $R_4$ form, with the nitrogen atom that bears them, a cyclic group, and $R_5$ is an ethyl group.

5. The device according to claim 1, wherein n is an integer ranging from 1 to 10,000.

6. The device according to claim 1, wherein $SiR_aR_b$—$[OSiR_aR_b]n$- of formula (I) is a unit derived from a linear silicone with a weight-average molecular mass (Mw) ranging from about 200 g/mol to about 40,000 g/mol.

7. The device according to claim 1, wherein the propellant is present in the composition, and the at least one polymer containing a silicone unit bearing alkoxy-(aminomethyl)-silyl functional groups is present in an amount ranging from about 0.1% to about 40% by weight, relative to the total weight of the composition.

8. The device according to claim 1, wherein the at least one cationic fixing polymer is chosen from the following polymers, alone or as mixtures:
 (1) homopolymers or copolymers derived from acrylic or methacrylic esters or amides and comprising at least one of the units of formula (A), (B), (C), and (D) below:

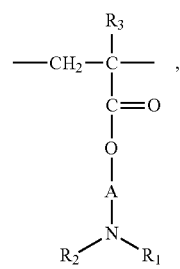

(A)

(B)

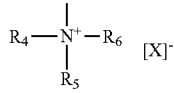

-continued

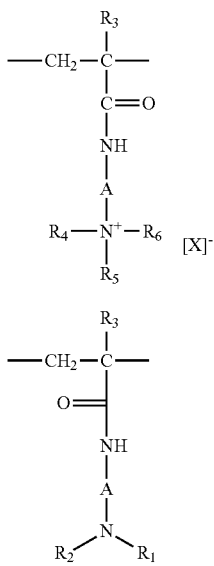

wherein:
R$_1$ and R$_2$, which may be identical or different from each other and in each formula, are chosen from a hydrogen atom or alkyl groups containing from 1 to 6 carbon atoms,
R$_3$, which may be identical or different in each formula, is chosen from a hydrogen atom or a CH$_3$ radical,
A, which may be identical or different in each formula, is chosen from a linear or branched alkyl group comprising from 1 to 6 carbon atoms or a hydroxyalkyl group comprising from 1 to 4 carbon atoms,
R$_4$, R$_5$, and R$_6$, which may be identical or different in each formula, are chosen from alkyl groups containing from 1 to 18 carbon atoms or a benzyl radical, and
X$^-$ is chosen from a methosulfate anion or a halide;
(2) cationic guar gums;
(3) quaternary copolymers of vinylpyrrolidone and of vinylimidazole;
(4) chitosans or salts thereof;
(5) cationic cellulose derivatives; or
(6) copolymers of vinylamine and of N-vinylformamide.

9. The device according to claim 1, wherein the at least one amphoteric fixing polymer is chosen from copolymers containing acidic vinyl units and basic vinyl units, cross-linked and acylated polyamino amides, polymers containing zwitterionic units, chitosan-based polymers, modified (C1-C5)alkyl vinyl ether/maleic anhydride copolymers, or polymers comprising units derived a) from at least one monomer chosen from acrylamides and methacrylamides substituted on the nitrogen atom with an alkyl group, b) from at least one acidic comonomer containing at least one reactive carboxylic group, and c) from at least one basic comonomer.

10. The device according to claim 1, wherein the at least one propellant is present in the composition, and the at least one amphoteric and/or cationic fixing polymer is present in an amount ranging from about 0.5% to about 20% by weight, relative to the total weight of the composition.

11. The device according to claim 1, wherein the composition further comprises at least one organic solvent chosen from alcohols, alkanes, esters, silicones, or mixtures thereof.

12. The device according to claim 11, wherein the propellant is present in the composition, and the at least one organic solvent is present in an amount ranging from about 10% to about 99.8% by weight, relative to the total weight of the composition.

13. The device according to claim 1, wherein the at least one propellant is present in the composition, and the composition further comprises water in an amount less than about 5% by weight, relative to the total weight of the composition.

14. The device according to claim 1, wherein the composition further comprises at least one catalyst, chosen from organic or mineral basic compounds, organic or mineral acids, or mixtures thereof.

15. The device according to claim 14, wherein the at least one propellant is present in the composition, and the at least one catalyst is present in an amount ranging from about 0.0001% to about 10% by weight, relative to the total weight of the composition.

16. The device according to claim 1, wherein the at least one propellant is chosen from compressed air, nitrogen, carbon dioxide, dimethyl ether, volatile hydrocarbons, chlorinated and/or fluorinated hydrocarbons, or mixtures thereof.

17. The device according to claim 1, wherein the at least one propellant is present in the composition in an amount ranging from about 10% to about 90% by weight, relative to the total weight of the composition.

18. A method for shaping and/or holding hair, wherein the method comprises using an aerosol device comprising:
a container, wherein the container comprises
at least one propellant; and
a hair composition, the composition comprising:
(i) at least one polymer containing a silicone unit bearing alkoxy-(aminomethyl)-silyl functional groups chosen from compounds according to formula (I) below:

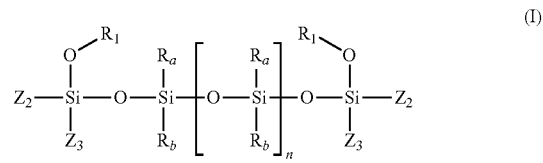

wherein:
Z$_2$ is chosen from —CH$_2$—NR$_3$R$_4$ groups;
Z$_3$ is chosen from OR$_5$ or R$_6$ groups;
R$_1$ is chosen from C$_1$-C$_6$ alkyl groups;
R$_3$ is chosen from a hydrogen atom or an R$_7$ group;
R$_4$ is chosen from C$_1$-C$_6$ alkyl groups or C$_5$-C$_6$ cycloalkyl groups; or R$_3$ and R$_4$, optionally form, with the nitrogen atom that bears them, a 5- to 8-membered heterocycle comprising from 1 to 3 heteroatoms;
R$_5$, R$_6$, and R$_7$, which may be identical or different, are chosen from C$_1$-C$_6$ alkyl groups;
R$_a$ and R$_b$, which may be identical or different, are chosen from C$_1$-C$_2$ alkyl groups; and
n is an integer greater than 1; and
(ii) at least one amphoteric fixing polymer and/or at least one cationic fixing polymer;
wherein the at least one propellant is present in the composition, or in the container, separate from the composition.

19. A cosmetic composition comprising:
(i) at least one polymer containing a silicone unit bearing alkoxy-(aminomethyl)-silyl functional groups chosen from compounds according to formula (I) below:

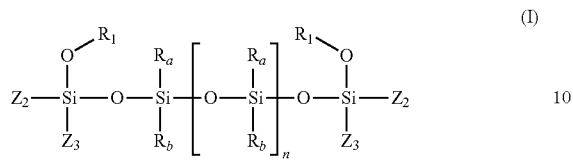

(I)

wherein:
$Z_2$ is chosen from $—CH_2—NR_3R_4$ groups;
$Z_3$ is chosen from $OR_5$ or $R_6$ groups;
$R_1$ is chosen from $C_1$-$C_6$ alkyl groups;
$R_3$ is chosen from a hydrogen atom or an $R_7$ group;
$R_4$ is chosen from $C_1$-$C_6$ alkyl groups or $C_5$-$C_6$ cycloalkyl groups; or $R_3$ and $R_4$, optionally form, with the nitrogen atom that bears them, a 5- to 8-membered heterocycle comprising from 1 to 3 heteroatoms;
$R_5$, $R_6$, and $R_7$, which may be identical or different, are chosen from $C_1$-$C_6$ alkyl groups;
$R_a$ and $R_b$, which may be identical or different, are chosen from $C_1$-$C_2$ alkyl groups; and
n is an integer greater than 1; and
(ii) at least one amphoteric fixing polymer and/or cationic fixing polymer.

* * * * *